US009945922B2

(12) United States Patent
Benner

(10) Patent No.: US 9,945,922 B2
(45) Date of Patent: Apr. 17, 2018

(54) DETERMINING A POSITION AND/OR A MOTION OF A PATIENT DURING A MEDICAL IMAGING EXAMINATION

(71) Applicant: Thomas Benner, Erlangen (DE)

(72) Inventor: Thomas Benner, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 694 days.

(21) Appl. No.: 14/485,723

(22) Filed: Sep. 13, 2014

(65) Prior Publication Data

US 2015/0077113 A1   Mar. 19, 2015

(30) Foreign Application Priority Data

Sep. 13, 2013  (DE) .................. 10 2013 218 432

(51) Int. Cl.
*G01R 33/565* (2006.01)
*G01R 33/26* (2006.01)
*G01R 33/30* (2006.01)
*G01R 33/385* (2006.01)
*G01B 11/00* (2006.01)
(Continued)

(52) U.S. Cl.
CPC ...... *G01R 33/56509* (2013.01); *A61B 5/0077* (2013.01); *A61B 5/721* (2013.01); *G01B 11/002* (2013.01); *G01P 13/00* (2013.01); *G01R 33/283* (2013.01); *G01R 33/307* (2013.01); *G01R 33/385* (2013.01); *A61B 5/055* (2013.01); *A61B 2034/2048* (2016.02);
(Continued)

(58) Field of Classification Search
CPC ............ G01R 33/56509; G01R 33/283; G01R 33/307; G01R 33/385; G01B 11/002; G01P 13/00; A61B 5/0077; A61B 5/721; A61B 2034/2048; A61B 2560/0223; A61B 2560/04; A61B 2562/0219
See application file for complete search history.

(56) References Cited

U.S. PATENT DOCUMENTS 6,329,821 B1    12/2001  Zhou
2004/0102695 A1*  5/2004  Stergiopoulos .... G01R 33/5673
                                                      600/413
(Continued)

FOREIGN PATENT DOCUMENTS

CN    101023878 A    8/2007
CN    101267770 A    9/2008
(Continued)

OTHER PUBLICATIONS

German Office Action cited in German Application No. 10 2013 218 432.8, dated Jun. 23, 2014, with English Translation.
(Continued)

*Primary Examiner* — Rodney Bonnette
(74) *Attorney, Agent, or Firm* — Lempia Summerfield Katz LLC

(57) ABSTRACT

A medical imaging apparatus includes a detector unit, a patient-receiving area at least partially surrounded by the detector unit, and a motion capture unit. The motion capture unit includes at least one first motion capture sensor for capturing patient monitoring data relating to a motion of the patient, and at least one second motion capture sensor for the capture of further motion data relating to a motion of the first motion capture sensor.

20 Claims, 4 Drawing Sheets

(51) Int. Cl.
*G01P 13/00* (2006.01)
*A61B 5/00* (2006.01)
*G01R 33/28* (2006.01)
*A61B 5/055* (2006.01)
*A61B 34/20* (2016.01)

(52) U.S. Cl.
CPC ... *A61B 2560/0223* (2013.01); *A61B 2560/04* (2013.01); *A61B 2562/0219* (2013.01)

(56) References Cited

U.S. PATENT DOCUMENTS

| | | |
|---|---|---|
| 2007/0041494 A1 | 2/2007 | Ruchala et al. |
| 2008/0081980 A1 | 4/2008 | Maschke et al. |
| 2011/0201916 A1 | 8/2011 | Duyn et al. |
| 2011/0216957 A1 | 9/2011 | Hsieh et al. |
| 2012/0085934 A1 | 4/2012 | Marcelis et al. |
| 2014/0073904 A1* | 3/2014 | Biber ............ A61B 6/527 600/410 |
| 2014/0073908 A1* | 3/2014 | Biber ............ G01R 33/56308 600/415 |
| 2014/0221812 A1* | 8/2014 | Heismann ........... A61B 5/055 600/407 |
| 2015/0241540 A1* | 8/2015 | Vernickel ......... G01R 33/56358 324/309 |

FOREIGN PATENT DOCUMENTS

| | | |
|---|---|---|
| CN | 102460205 A | 5/2012 |
| DE | 60038427 T2 | 4/2009 |
| DE | 102009010592 B4 | 9/2014 |
| EP | 2594197 A1 | 5/2013 |
| JP | H0919413 A | 1/1997 |
| JP | 2004201977 A | 7/2004 |
| KR | 20120096728 A | 8/2012 |
| WO | WO2009129457 A1 | 10/2009 |
| WO | WO2012160486 A3 | 1/2013 |

OTHER PUBLICATIONS

Chinese Office Action for related Chinese Application No. 2014104663475 dated Jun. 29, 2016 with English Translation.
Korean Office Action for related Korean Application No. 10-2014-0119031 dated May 23, 2016.
Korean office Action for related Korean Application No. 10-2014-0119031 dated Jan. 13, 2016, with English Translation.

* cited by examiner

FIG 2
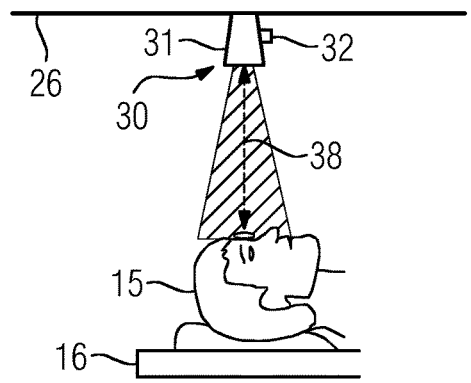
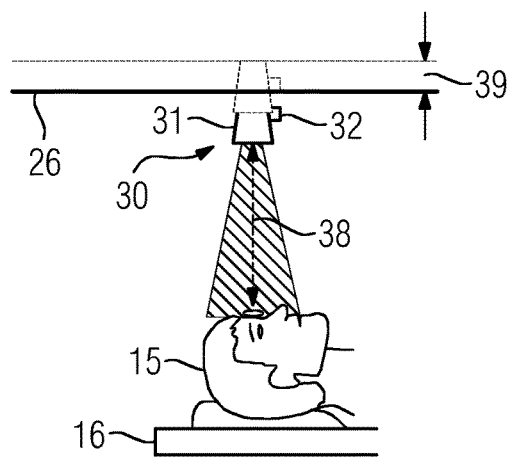
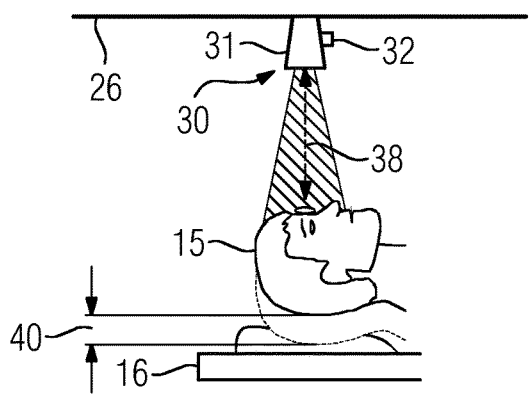

DETERMINING A POSITION AND/OR A MOTION OF A PATIENT DURING A MEDICAL IMAGING EXAMINATION

This application claims the benefit of DE 10 2013 218 432.8, filed on Sep. 13, 2013, which is hereby incorporated by reference in its entirety.

BACKGROUND

For medical imaging examinations (e.g., magnetic resonance examinations), medical imaging apparatuses (e.g., magnetic resonance apparatuses) include a motion capture sensor, by which patient monitoring data for capturing a motion and/or of a change of position of the patient during the medical imaging examination is captured. Captured patient monitoring data is used to correct the image data captured during the medical imaging examination with respect to a motion of the patient. The captured patient monitoring data may also be used for a prospective correction of a data acquisition, such as, for example, during a magnetic resonance examination, to track gradients.

If, in this case, the motion capture sensor is arranged on a moving component of the medical imaging apparatus, the motion capture sensor arranged on the component also moves together with the component and/or vibrates together with the component due to vibrations of the component. This may result in unwanted errors on the capture of the motion and/or on the capture of the change of position of the patient.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a patient motion may be captured exactly during a medical imaging examination.

In one embodiment, a medical imaging apparatus (e.g., a magnetic resonance apparatus) includes a detector unit, a patient-receiving area at least partially surrounded by the detector unit, and a motion capture unit. The motion capture unit includes at least one first motion capture sensor for capturing patient monitoring data relating to a motion of the patient.

The motion capture unit includes at least one further motion capture sensor for capturing further motion data relating to a motion of the first motion capture sensor. A motion (e.g., a vibration) of the first motion capture sensor may be captured, and therefore, the captured patient monitoring data may be advantageously corrected. This enables a motion of the patient to be captured particularly exactly and unwanted errors during the capture of the patient monitoring data to be advantageously avoided. This enables particularly exact localization of the patient in dependence on time using the motion capture unit during a medical imaging examination (e.g., a magnetic resonance examination). For example, during a magnetic resonance examination, despite the occurrence of vibrations in a housing wall surrounding the patient-receiving area, the first motion capture sensor inside a patient-receiving area (e.g., on the housing wall) may remain arranged for the capture of the patient monitoring data so that a direct and as complete as possible capture of a patient motion may be achieved. The at least one further motion capture sensor may be decoupled from movements and/or vibrations of the at least one first motion capture sensor, such as, for example, a camera, arranged on a wall for monitoring a motion of the at least one first motion capture sensor. In addition, the at least one further motion capture sensor may be arranged inside the medical imaging apparatus such that the at least one further motion capture sensor experiences the same motion (e.g., vibrations) as the at least one first motion capture sensor.

The at least one first motion capture sensor may be formed by a conventional motion capture sensor, such as, for example, a camera (e.g., a 3D camera for capturing three-dimensional patient monitoring data, an infrared camera for capturing infrared patient monitoring data, an ultraviolet camera for capturing ultraviolet patient monitoring data, another motion capture sensor, or any combination thereof). The patient monitoring data is, for example, formed by three-dimensional patient monitoring data. In addition, the motion capture unit may include more than one first motion capture sensor. The motion capture sensors may each be embodied the same or may be embodied differently.

In one embodiment, the at least one further motion capture sensor includes an acceleration sensor. This enables movements and/or vibrations of the first motion capture sensor to be captured directly based on the transmission of these movements and/or vibrations to the acceleration sensor. This also enables optical capturing of motion data relating to a motion and/or vibration of the first motion capture sensor to be dispensed with so that the erroneous capture of further motion data relating to a motion and/or vibration of the first motion capture sensor may be avoided. The erroneous capture of the further motion data may be caused by interfering objects arranged inside an optical axis and/or a beam axis of the at least one further motion capture sensor. In one embodiment, the acceleration sensor captures movements and/or vibrations along three different spatial axes aligned orthogonally with respect to one another.

In one embodiment, the at least one first motion capture sensor and the at least one further motion capture sensor may be arranged inside the patient-receiving area, thus enabling the direct capture of a motion of the first motion capture sensor. In one embodiment, the at least one further motion capture sensor is a camera to achieve an unimpeded view of the first motion capture sensor. The further motion capture sensor may include an acceleration sensor and hence may be arranged inside the patient-receiving area such that the acceleration sensor experiences the same motion as the at least one first motion sensor. In an alternative embodiment, the at least one first motion capture sensor and/or the at least one further motion capture sensor may also to be arranged outside the patient-receiving area.

The at least one further motion capture sensor may be arranged on the same component as the first motion capture sensor. In this case, movements and/or vibrations in this component, which are transmitted by this component onto the first motion capture sensor, may also be transmitted directly to the at least one further motion capture sensor and captured directly there. In one embodiment, in this case, the at least one further motion capture sensor includes an acceleration sensor.

In one embodiment, the at least one further motion capture sensor may be arranged directly on the first motion capture sensor, thus enabling movements and/or vibration changes of the first motion capture sensor to be transmitted directly to the at least one further motion capture sensor for the capture of further motion data relating to a motion and/or change of position of the first motion capture sensor. In one embodiment, the at least one further motion capture sensor includes an acceleration sensor.

In one embodiment, the at least one further acceleration sensor may be arranged inside the patient-receiving area such that a capture direction of the further motion capture sensor coincides with a spatial direction of the detector unit and/or of the first motion capture sensor. This advantageously enables complex calibration of the at least one further acceleration sensor (e.g., of a coordinate system implemented inside the acceleration sensor) to be dispensed with. For example, a particularly time-saving and quick evaluation of the motion data of the at least one further acceleration sensor together with the patient monitoring data of the first acceleration sensor may be provided. In addition, a particularly time-saving and quick evaluation of the motion data of the at least one further acceleration sensor together with magnetic resonance data from the detector unit may be achieved.

In one embodiment, the motion capture unit includes a calibration unit for calibrating a coordinate system of the further acceleration sensor with a coordinate system of the first acceleration sensor and/or a coordinate system of the detector unit. This enables a coordinate system of the at least one further motion capture sensor, on which the capture of the further motion data is based, to be adapted to a coordinate system of the first motion capture sensor and/or the detector unit in a simple way. In one embodiment, the calibration unit compiles a transformation specification.

In an advantageous development, the motion capture unit includes an evaluation unit configured to determine motion correction data relating to a motion of the first motion capture sensor with reference to the further motion data captured by the further motion capture sensor. This enables the motion correction data relating to the motion of the first motion capture sensor to be determined and made available for a further evaluation of the patient monitoring data and/or of magnetic resonance data in a time-saving way. In addition, the evaluation unit may also be configured to determine or calculate a position and/or motion of the patient. The evaluation unit takes into account the determined and/or calculated motion correction data of a change of position and/or of the motion of the first motion capture sensor for a calculation and/or a determination of the motion and/or position of the patient. This enables exact motion data relating to the patient to be available for further data evaluation and/or further data capture in a time-saving way.

In this case, motion correction data of the first motion capture sensor may be information as to whether the first motion capture sensor has executed a motion and/or a change of position. In addition, if a motion and/or a change of position of the first motion capture sensor have been executed, the motion correction data of the first motion capture sensor also includes a time dependence of the motion data of the first motion capture sensor. In one embodiment, the first motion capture sensor and the further motion capture sensor are synchronized with respect to a capture time thus facilitating simple correction of the patient monitoring data.

A compact motion capture unit may be achieved if the evaluation unit is encompassed by the first motion capture sensor. In addition, simple and quick data transmission of motion data relating to the patient that has already been corrected may be achieved, since this motion data that has already been corrected has a lower data volume than the unevaluated patient monitoring data, for example, in the form of video data. For example, the corrected motion data includes translation data and/or rotation data relating to a translation and/or a rotation, for example, of a region of the patient's body to be examined in dependence on time. This facilitates simple assignment of the motion data to magnetic resonance data for a retrospective and/or prospective evaluation and/or correction of the magnetic resonance data.

One or more of the present embodiments also relate to a method for capturing a motion of a patient during a medical imaging examination using a medical imaging apparatus (e.g., a magnetic resonance apparatus). The method includes capturing patient monitoring data using a first motion capture sensor and capturing further motion data using a further motion capture sensor. The method also includes determining motion correction data of the first motion capture sensor with reference to the further motion data, and determining corrected motion data relating to the patient with reference to the first patient monitoring data and with reference to the determined motion correction data of the first motion capture sensor.

In this case, a change of position and/or a motion (e.g., a vibration) of the first motion capture sensor may be captured, and the patient monitoring data relating to a motion of the patient is thus corrected. Exact localization of the patient in dependence of time using the motion capture unit may be provided. In addition, this enables simple assignment of the motion data to magnetic resonance data for a retrospective and/or prospective evaluation and/or correction of the magnetic resonance data. In addition, simple and quick data transmission motion data relating to the patient that has already been corrected may be achieved, since this motion data that has already been corrected has a lower data volume than the unevaluated patient monitoring data, for example, in the form of video data.

In addition, corrected motion data relating to the patient may, for example, be the patient monitoring data captured by the first motion capture sensor. A correction of the patient monitoring data using the motion correction data has taken place. In one embodiment, the first motion capture sensor and the further motion capture sensor are synchronized with respect to a capture time.

In one embodiment, a coordinate system of the at least one further motion capture sensor may be calibrated with respect to a coordinate system of the first motion capture sensor and/or a detector unit of the medical imaging apparatus. This enables a coordinate system of the at least one further motion capture sensor, on which the capture of the further motion data is based, to be adapted to a coordinate system of the first motion capture sensor and/or the detector unit. This enables data evaluation of the further motion data and the patient monitoring data to be performed in a simplified and time-saving way. In addition, a time-saving evaluation of medical examination data may be provided by the corrected motion data relating to the patient.

One or more of the present embodiments may also relate to a computer program that may be loaded directly into a memory (e.g., a non-transitory computer-readable storage medium) of a programmable evaluation unit of a motion capture unit and/or a medical imaging apparatus, with programming (e.g., instructions) for executing a method for capturing a motion of the patient during a medical imaging examination (e.g., a medical magnetic resonance examination) when the computer program in the non-transitory computer-readable storage medium is executed. A software implementation of this kind has the advantage that existing evaluation units of motion capture units and/or of magnetic resonance appliances are modified in a suitable manner by the implementation of the computer program in order to capture a motion of a patient as exactly as possible in the way described by the present embodiments.

BRIEF DESCRIPTION OF THE DRAWINGS

FIG. 2 shows a detailed view of an exemplary capture of a patient motion by a motion capture unit with different positions of a first motion capture sensor and hypothetical motion of a patient;

DETAILED DESCRIPTION

Figure 1:
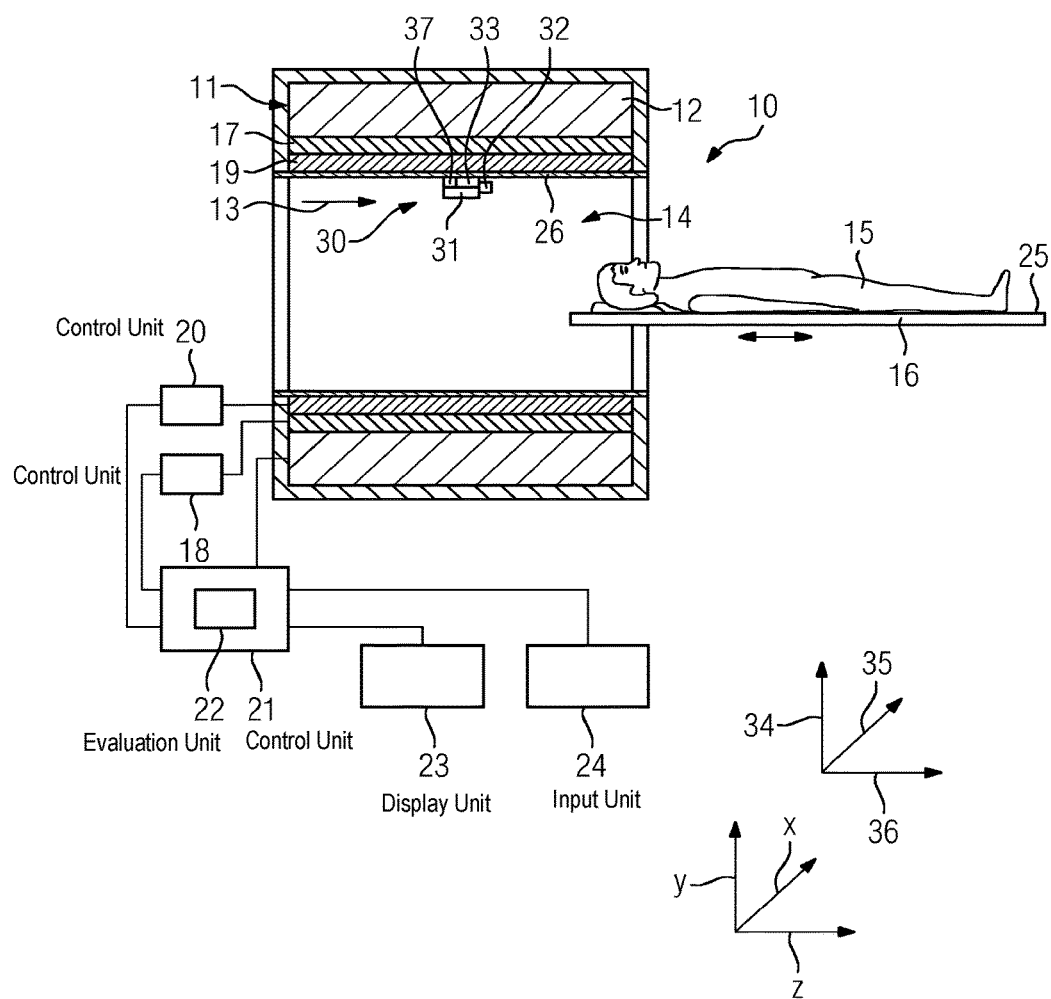
FIG. 1 shows one embodiment of a medical imaging apparatus with a motion capture unit.

FIG. 1 is a schematic representation of one embodiment of a medical imaging apparatus that is formed by a magnetic resonance apparatus 10. The medical imaging apparatus is not restricted to a magnetic resonance apparatus 10. Other embodiments of the medical imaging apparatus may be provided.

The magnetic resonance apparatus 10 includes a detector unit formed by a magnetic unit 11 having a main magnet 12 for generating a strong and, for example, constant main magnetic field 13. The magnetic resonance apparatus 10 also includes a cylindrical patient-receiving area 14 for receiving a patient 15. The patient-receiving area 14 is cylindrically enclosed by the magnetic unit 11 in a circumferential direction. An embodiment of the patient-receiving area 14 differs from this may be provided. The patient 15 may be pushed into the patient-receiving area 14 using a patient support apparatus 16 of the magnetic resonance apparatus 10. The patient support apparatus 16 is arranged movably inside the cylindrical patient-receiving area 14.

The magnetic unit 11 also includes a gradient coil unit 17 for generating magnetic field gradients. The gradient coil unit 17 is used for spatial encoding during imaging. The gradient coil unit 17 is controlled by a gradient control unit 18. The magnetic unit 11 also includes a high-frequency antenna unit 19 and a high-frequency antenna control unit 20 for exciting polarization that is established in the main magnetic field 13 generated by the main magnet 12. The high-frequency antenna unit 19 is controlled by the high-frequency antenna control unit 20 and irradiates high-frequency magnetic resonance sequences in an examination chamber, which is substantially formed by the patient-receiving area 14.

For controlling the main magnet 12, the gradient control unit 18, and for controlling the high-frequency antenna control unit 20, the magnetic resonance apparatus 10 includes a system control unit 21 formed by a computing unit. The system control unit 21 centrally controls the magnetic resonance apparatus 10 such as, for example, the execution of a predetermined imaging gradient echo sequence. The system control unit 21 also includes an evaluation unit 22 for evaluating magnetic resonance image data. Control information such as, for example, imaging parameters and reconstructed magnetic resonance images may be displayed on a display unit 23, for example, on at least one monitor of the magnetic resonance apparatus 10 for an operator. In addition, the magnetic resonance apparatus 10 includes an input unit 24 using which an operator may input information and/or parameters during a measuring process.

The magnetic resonance apparatus 10 also includes a motion capture unit 30 for capturing a motion of the patient 15. During a magnetic resonance examination, using the motion capture unit 30, patient monitoring data relating to a patient 15 positioned inside the patient-receiving area 14 is captured, and this motion data is taken account during a capture of the magnetic resonance data and/or an evaluation of the captured magnetic resonance data, for example, in the form of a retrospective and/or prospective motion correction.

The motion capture unit 30 includes a first motion capture sensor 31 and a further motion capture sensor 32 (e.g., a second motion capture sensor). In this case, the first motion capture sensor 31 is arranged inside the patient-receiving area 14 of the magnetic resonance apparatus 10. The first motion capture sensor 31 is arranged on an inner side of a housing wall 26 of the magnetic unit 11 surrounding the patient-receiving area 14 facing a support surface 25 of the patient support apparatus 16. In one embodiment, the first motion capture sensor 31 is arranged on the housing wall 26 on a side opposite the support surface 25.

In an alternative embodiment, the motion capture unit 30 may include more than a first motion capture sensor 31 (e.g., a plurality of first motion capture sensors). The plurality of first motion capture sensors 31 may be arranged at different positions on the inner side of the housing wall 26. In addition, in an alternative embodiment, the at least one first motion capture sensor 31 may also be arranged outside the patient-receiving area 14.

The first motion capture sensor 31 is configured for capturing first motion data relating to a motion of the patient 15 during the magnetic resonance examination. The first motion data is formed by patient monitoring data. The first motion capture sensor 31 is formed by a conventional motion capture sensor 31 such as, for example, by a camera (e.g., a 3D camera) for capturing three-dimensional patient monitoring data, by an infrared camera for capturing infrared patient monitoring data, by a camera for capturing ultraviolet patient monitoring data, by another first motion capture sensor 31, or any combination thereof.

The further motion capture sensor 32 of the motion capture unit 30 is configured to capture further motion data relating to a motion of the first motion capture sensor 31. The further motion capture sensor 32 is also arranged inside the patient-receiving area 14.

In one embodiment, the further motion capture sensor 32 includes an acceleration sensor that, to capture the further motion data, captures an acceleration acting on the first motion capture sensor 31 and/or acting on the further acceleration sensor 32. The further motion capture sensor 32 is arranged directly on the first motion capture sensor 31 so that a motion of the first motion capture sensor 31 is also transmitted directly to the further motion capture sensor 32 and may be captured thereby. The further motion data captured by the further motion capture sensor 32 thus contains motion information relating to the motion of the first motion capture sensor 31.

In an alternative embodiment, the further motion capture sensor 32 may be different than an acceleration sensor. In addition, in an alternative embodiment, the motion capture unit 30 may include more than one further motion capture sensor 32. For example, a number of further motion capture sensors 32 may be coupled to a number of first motion capture sensors 31.

The motion capture unit 30 also includes an evaluation unit 33. The evaluation unit 33 is configured to determine motion correction data relating to a motion of the first motion capture sensor 31 with reference to the further motion data captured by the further motion capture sensor 32. In this case, the evaluation unit 33 is encompassed by the first motion capture sensor 31. Data transmission between the evaluation unit 33, the first motion capture sensor 31 and the further motion capture sensor 32 takes place via a data transmission unit (not shown in more detail). The arrangement of the evaluation unit 33 inside the motion capture unit 30 (e.g., inside the first motion capture sensor 31) enables quick evaluation of the first motion data and/or the further motion data. The evaluation unit 33 transmits data that has already been evaluated by the motion capture unit (e.g., corrected motion data relating to the patient), which substantially corresponds to corrected patient monitoring data, to the evaluation unit 22 and/or further units of the system control unit 21. Transmission of the data that has already been evaluated also uses low bandwidth. Data transmission between the evaluation unit 33 and the system control unit 21 takes place via a data transmission unit (not shown in any more detail).

For the evaluation of the first and/or further motion data, the evaluation unit 33 includes software and/or computer programs for the evaluation of the first and/or further captured motion data that may be loaded in a processor of the evaluation unit 33 and includes programming for performing the evaluation of the first and/or further captured motion data.

As an alternative, an arrangement of the evaluation unit 33 inside the further motion capture sensor 32 may also be provided. In addition, the evaluation of the first and/or further motion data captured by the motion capture unit 30 may also to be implemented by the evaluation unit 22 of the system control unit 21 and/or further evaluation units of the magnetic resonance apparatus 10. However, an evaluation of the first and/or further motion data by the evaluation unit 22 of the system control unit 21 would use a larger bandwidth for a data transmission for the transmission of video data from the motion capture unit 30 to the evaluation unit 22 than the bandwidth used for the transmission of motion data that has already been evaluated.

In this case, the further motion capture sensor 32 (e.g., the acceleration sensor) is configured to capture an acceleration along three capture directions 34, 35, 36. The further motion capture sensor 32 is arranged inside the patient-receiving area 14 (e.g., on the first motion capture sensor 31), such that the three capture directions 34, 35, 36 of the further motion capture sensor 32 each correspond to a spatial direction x, y, z of the magnetic unit 11 and/or spatial directions and/or capture directions in a coordinate system of the first motion capture sensor 31. In this case, the two spatial directions x, y fix an entrance hole of the patient-receiving area, and the spatial direction z corresponds to a direction of travel of the patient support apparatus 16 and/or a direction of entry during an entry process of the patient support apparatus 16 into the patient-receiving area 14. The three capture directions 34, 35, 36 of the further motion capture sensor 32 may each correspond to one of the spatial directions and/or capture directions of the first motion capture sensor 31, and each corresponds to one of the spatial directions x, y, z of the magnetic unit 11.

In addition, the motion capture unit 30 includes a calibration unit 37, by which calibration of a coordinate system of the further motion capture sensor 32 (e.g., the three capture directions 34, 35, 36 of the further motion capture sensor 32) with the coordinate system of the magnetic unit 11 (e.g., the three spatial directions x, y, z of the magnetic unit 11) is performed. In this case, the calibration unit 37 generates a transformation specification that is applied to the motion data captured by the further motion capture sensor 32 so that the transformed further motion data is compatible with the coordinate system of the magnetic unit 11 for a motion correction of the magnetic resonance data. Calibration by the calibration unit 37 may be performed once and is stored in a memory unit (not shown in any more detail).

Alternatively or additionally, the calibration unit 37 may be configured to harmonize the coordinate system of the further motion capture sensor 32 with a coordinate system of the first motion capture sensor 31 in that a transformation specification is compiled for the three capture directions 34, 35, 36 of the further motion capture sensor 32. This provides that these three capture directions 34, 35, 36 of the further motion capture sensor 32 are compatible and/or in conformity with the three capture directions of the first motion capture sensor 31.

In one embodiment, the calibration unit 37 is encompassed by the evaluation unit 33. Alternatively, the calibration unit 37 may also be embodied separately from the evaluation unit 33.

FIGS. 2a to 2c each show one embodiment of an arrangement of the motion capture unit 30 on the side of the housing wall 26 opposite the support surface 25 with different positions of the housing wall 26 with respect to a position of the patient 15 (FIGS. 2a and 2b). This may also be interpreted as hypothetical movements of the patient 15 (FIG. 2c). In FIGS. 2a to 2c, the change of a position of the first motion capture sensor 31 is shown one-dimensionally. However, the change of position of the first motion capture sensor 31 is restricted to one dimension and should be understood as being exemplary for all three spatial directions.

In FIG. 2a, the housing wall 26 is shown in an idle state. In this idle state of the housing wall 26, a distance 38 between the patient 15 and the first motion capture sensor 31 remains constant and/or the same. In this case, a change in the distance 38 between the patient 15 and the first motion capture sensor 31 would result from a motion of the patient 15 that may be captured by the first motion capture sensor 31.

In FIG. 2b, the housing wall 26 has undergone a change of position 39, which is, for example, due to vibrations and/or due to oscillations transmitted to the housing wall 26. In this case, the distance 38 between the patient 15 and the first motion capture sensor 31 changes by the value of the change of position 39. In FIG. 2b, the change of position 39 (e.g., the vibrations) of the housing wall 26 is shown by way of example as a shortened distance 38 between the housing wall 26 and the patient 15. This shortened distance 38 between the patient 15 and the housing wall 26 is captured by the first motion capture sensor 31 in that the motion of the first motion capture sensor is transmitted directly to the further motion capture sensor.

Without the information from the further motion capture sensor 32, this change of position 39 (e.g., the vibrations and/or oscillations) of the housing wall 26 would be interpreted as a motion 40 of the patient 15 in the direction of the housing wall 26 (FIG. 2c). However, this change of position 39 of the housing wall 26, which, due to the arrangement of the first motion capture sensor 31 together with the further motion capture sensor 32 on the housing wall 26, is also executed by the first motion capture sensor 31 and the further motion capture sensor 32, is captured by the further motion capture sensor 32. During an evaluation of the first motion data, (e.g., the patient monitoring data), the evaluation unit 33 takes into account the further motion data captured by the further motion capture sensor 32 so that vibrations or further position changes 39 executed by the housing wall 26 are recognized as such with reference to the further motion data. With reference to the determined motion of the first motion capture sensor 31, the evaluation unit 33 performs a correction of the captured patient monitoring data in that corrected motion data relating to the patient 15 is provided.

In one embodiment, the magnetic resonance apparatus 10 may include further components that magnetic resonance appliances usually include. A general mode of operation of a magnetic resonance apparatus 10 is also known to the person skilled in the art so that a detailed description of the general components is dispensed with.

Figure 3:
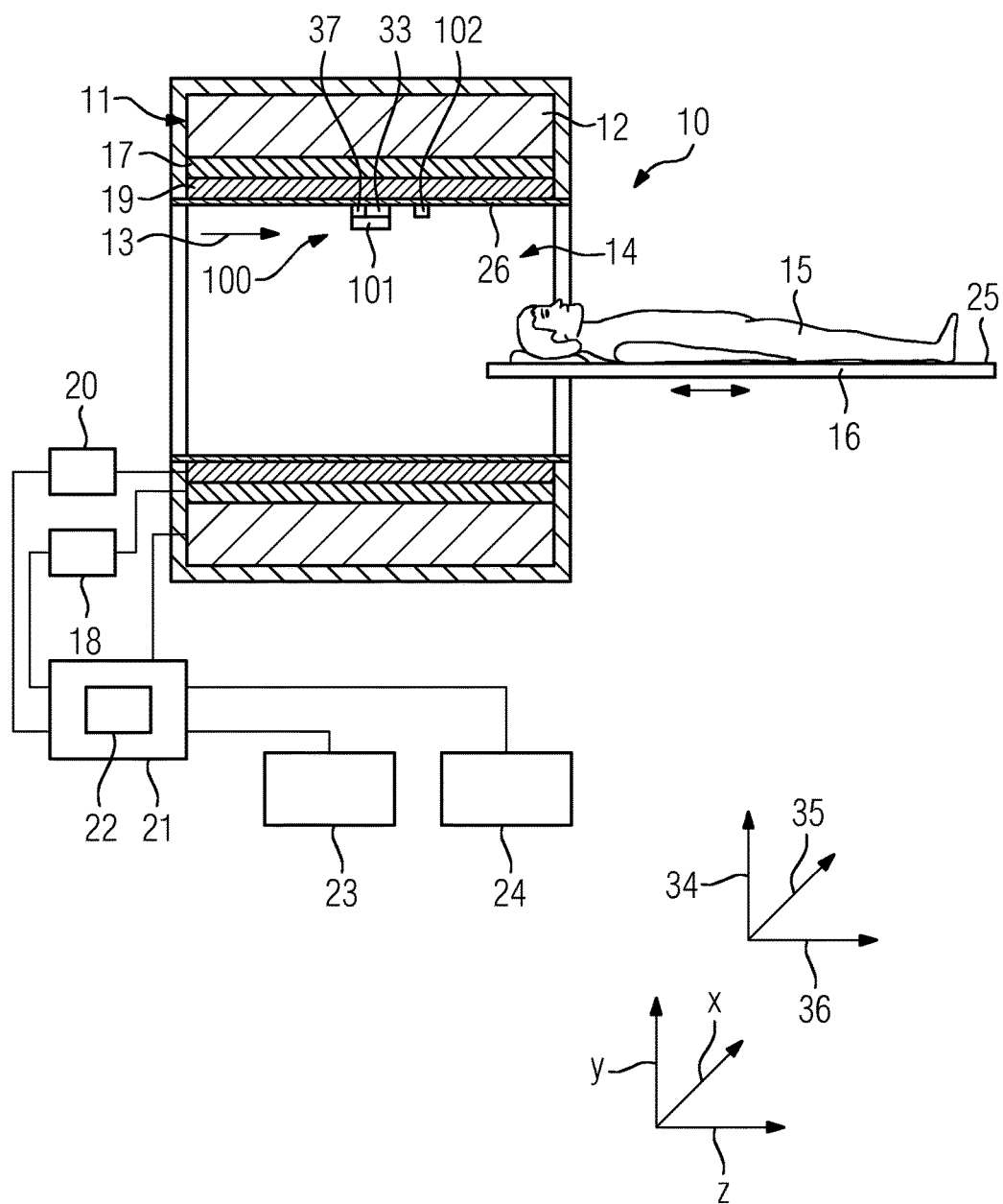
FIG. 3 shows an alternative embodiment of the motion capture unit in FIG. 1.

FIG. 3 shows an alternative exemplary embodiment of the motion capture unit. Substantially same components, features and functions are designated with the same reference number. The following description is substantially restricted to the differences from the exemplary embodiments in FIGS. 1 to 2c, where with respect to same components, features and functions, reference is made to the description of the exemplary embodiments in FIGS. 1 to 2c.

Similarly to the statements relating to the exemplary embodiments in FIGS. 1 to 2c, the motion capture unit 100 in FIG. 3 includes a first motion capture sensor 101 configured to capture first motion data formed by patient monitoring data relating to a motion of a patient 15. The motion capture unit 100 also includes a further motion capture sensor 102 configured to capture further motion data relating to a motion of the first motion capture sensor 101. An embodiment of the first motion capture sensor 101 and an arrangement of the first motion capture sensor 101 inside the magnetic resonance apparatus 10 correspond to the statements relating to the exemplary embodiment in FIG. 1.

In one embodiment, the further motion capture sensor 102 is also formed by an acceleration sensor and arranged inside the patient-receiving area 14 of the magnetic resonance apparatus 10. The further motion capture sensor 102 is arranged on a same component as the first motion capture sensor 101 inside the patient-receiving area 14. In one embodiment, both the first motion capture sensor 101 and the further motion capture sensor 102 are arranged on the side of the housing wall 26 facing the support surface 25.

In this case, the further motion capture sensor 102 may be arranged on the housing wall 26 at a short distance from the first motion capture sensor 101 so that the same acceleration and/or motion acts on the further motion capture sensor 102 as on the first motion capture sensor 101. In one embodiment, a distance between the two motion capture sensors 101, 102 is maximum 20 cm, maximum 10 cm, or maximum 5 cm.

In an alternative embodiment, the further motion capture sensor 102 may also be attached out of the sight of the patient 15 on the side of the housing wall 26 facing the high-frequency antenna unit 19.

The further embodiment of the motion capture unit 30 corresponds to the statements relating to the exemplary embodiments in FIGS. 1 to 2c.

Figure 4:
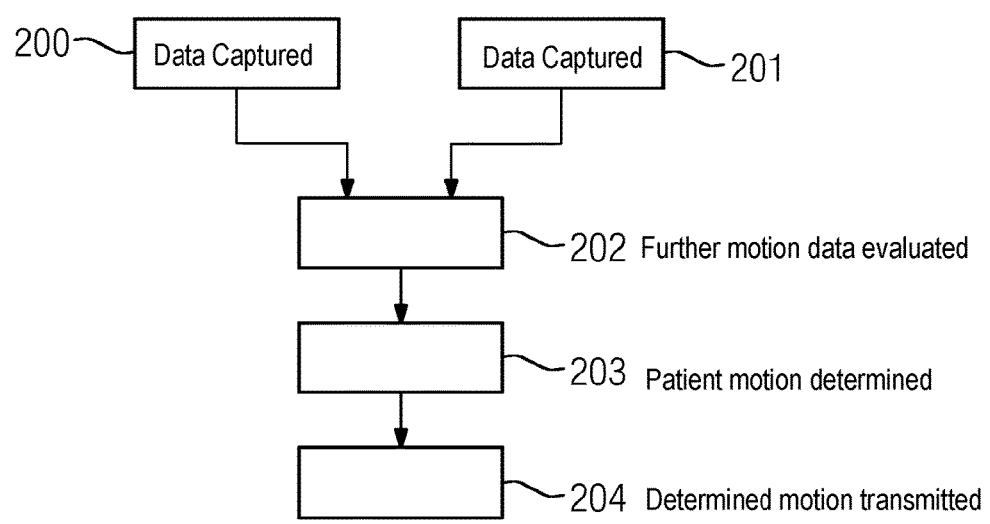
FIG. 4 shows a flow diagram of one embodiment of a method for capturing a motion of a patient during a medical imaging examination.

FIG. 4 is a schematic representation of a flow diagram of one embodiment of a method for capturing a motion of the patient 15 during a medical imaging examination (e.g., a medical magnetic resonance examination). The motion of the patient 15 during the magnetic resonance examination is captured by the motion capture unit 30, 100 of the magnetic resonance apparatus 10.

In act 200, patient monitoring data is captured by the first motion capture sensor 31, 101 and transmitted to the evaluation unit 33 of the motion capture unit 30, 100. Simultaneously, in act 201, the further motion data is captured by the further motion capture sensor 32, 102. For a simultaneous capture of the patient monitoring data by the first motion capture sensor 31 and the further motion data by the further motion capture sensor 32, the two motion capture sensors 31, 32 are synchronized. The further motion data of the further motion capture sensor 32, 102 is also transmitted to the evaluation unit 33 of the motion capture unit 30, 100.

The evaluation unit 33 initially evaluates the further motion data in act 202 with respect to a motion of the first motion capture sensor 31, 101 and determines a motion in the form of motion correction data of the first motion capture sensor 31, 101. In this case, the motion correction data includes the type of the motion of the first motion capture sensor 31, 101 and/or also a period of the motion of the first motion capture sensor 31, 101. In act 203, the evaluation unit 33 determines a motion of the patient 15 in the form of corrected motion data with reference to the patient monitoring data and with reference to the determined motion correction data of the first motion capture sensor 31, 101.

If necessary, act 202 for the evaluation of the further motion data also includes a calibration of the further motion data in order to achieve conformity and/or compatibility between the coordinate system of the further motion data and the coordinate system, the three spatial axes x, y, z of the magnetic unit 11, a coordinate system, the spatial axes of the first motion capture sensor, or any combination thereof.

In act 204, the evaluation unit 33 transmits the motion determined (e.g., the corrected motion data) relating to the patient 15 with reference to the patient monitoring data and with reference to the motion correction data of the first motion capture sensor 31, 101 to the system control unit 21 of the magnetic resonance apparatus 10 via a data transmission unit (not shown in further detail). The corrected motion data is made available at the system control unit 21 for an evaluation and prospective correction of the magnetic resonance data.

To enable evaluation of the further motion data and the patient monitoring data, the evaluation unit 33 includes a processor unit and software and/or computer programs required for the evaluation. The software and/or computer programs are stored directly in a memory unit (e.g., a non-transitory computer-readable storage medium; not shown in further detail) of the programmable evaluation unit 33. In one embodiment of the computer programs and/or the software in the evaluation unit 33, the method for capturing a motion of the patient 15 is performed during a medical imaging examination (e.g., a medical magnetic resonance examination).

Although the invention is illustrated and described in more detail by the exemplary embodiments, the invention is not restricted by the disclosed examples, and other variations may be derived herefrom by the person skilled in the art without departing from the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A medical imaging apparatus comprising:
a detector unit;
a patient-receiving area at least partially surrounded by the detector unit; and
a motion capture unit comprising at least one first motion capture sensor for capturing patient monitoring data relating to a motion of a patient,
wherein the motion capture unit comprises at least one second motion capture sensor for capturing further motion data of a motion of the first motion capture sensor.

2. The medical imaging apparatus of claim 1, wherein the at least one first motion capture sensor and the at least one second motion capture sensor are arranged inside the patient-receiving area.

3. The medical imaging apparatus of claim 1, wherein the at least one second motion capture sensor is arranged on a same component as the at least one first motion capture sensor.

4. The medical imaging apparatus of claim 1, wherein the at least one second motion capture sensor is arranged directly on the at least one first motion capture sensor.

5. The medical imaging apparatus of claim 1, wherein the at least one second motion capture sensor, which is inside the patient-receiving area, is arranged such that a capture direction of the at least one second motion capture sensor coincides with a spatial direction of the detector unit, the at least one first motion capture sensor, or the detector unit and the at least one first motion capture sensor.

6. The medical imaging apparatus of claim 1, wherein the motion capture unit comprises a calibration unit for calibration of a coordinate system of the at least one second motion capture sensor with a coordinate system of the at least one first motion capture sensor, a coordinate system of the detector unit, or the coordinate system of the at least one first motion capture sensor and the coordinate system of the detector unit.

7. The medical imaging apparatus of claim 1, wherein the motion capture unit comprises an evaluation unit configured to determine motion correction data of motion of the at least one first motion capture sensor with reference to further motion data captured by the at least one second motion capture sensor.

8. The medical imaging apparatus of claim 7, wherein the evaluation unit is comprised by the at least one first motion capture sensor.

9. The medical imaging apparatus of claim 1, wherein the at least one second motion capture sensor comprises an acceleration sensor.

10. The medical imaging apparatus of claim 9, wherein the at least one first motion capture sensor and the at least one second motion capture sensor are arranged inside the patient-receiving area.

11. The medical imaging apparatus of claim 10, wherein the at least one second motion capture sensor is arranged on a same component as the at least one first motion capture sensor.

12. The medical imaging apparatus of claim 11, wherein the at least one second motion capture sensor is arranged directly on the at least one first motion capture sensor.

13. The medical imaging apparatus of claim 12, wherein the at least one second motion capture sensor is arranged such that a capture direction of the at least one second motion capture sensor coincides with a spatial direction of the detector unit, the at least one first motion capture sensor, or the detector unit and the at least one first motion capture sensor.

14. The medical imaging apparatus of claim 13, wherein the motion capture unit comprises a calibration unit for calibration of a coordinate system of the at least one second motion capture sensor with a coordinate system of the at least one first motion capture sensor, a coordinate system of the detector unit, or the coordinate system of the at least one first motion capture sensor and the coordinate system of the detector unit.

15. The medical imaging apparatus of claim 14, wherein the motion capture unit comprises an evaluation unit configured to determine motion correction data of motion of the at least one first motion capture sensor with reference to further motion data captured by the at least one second motion capture sensor.

16. The medical imaging apparatus of claim 15, wherein the evaluation unit is comprised by the at least one first motion capture sensor.

17. A method for capturing a motion of a patient during a medical imaging examination using a medical imaging apparatus, the method comprising:
capturing patient monitoring data using a first motion capture sensor;
capturing further motion data using a second motion capture sensor;
determining motion correction data of the first motion capture sensor with reference to the further motion data; and
determining corrected motion data relating to the patient with reference to the first patient monitoring data and with reference to the determined motion correction data of the first motion capture sensor.

18. The method of claim 17, wherein a coordinate system of the second motion capture sensor is calibrated with respect to a coordinate system of the first motion capture sensor, a coordinate system of a detector unit of the medical imaging apparatus, or the coordinate system of the first motion capture sensor and the coordinate system of the detector unit.

19. In a non-transitory computer-readable storage medium that stores instructions executable by an evaluation unit of a motion capture unit, a medical imaging apparatus, or a combination thereof to capture a motion of a patient during a medical imaging examination using the medical imaging apparatus, the instructions comprising:
capturing patient monitoring data using a first motion capture sensor;
capturing further motion data using a second motion capture sensor;
determining motion correction data of the first motion capture sensor with reference to the further motion data; and
determining corrected motion data relating to the patient with reference to the first patient monitoring data and with reference to the determined motion correction data of the first motion capture sensor.

20. The non-transitory computer-readable storage medium of claim 19, wherein a coordinate system of the second motion capture sensor is calibrated with respect to a coordinate system of the first motion capture sensor, a coordinate system of a detector unit of the medical imaging apparatus, or the coordinate system of the first motion capture sensor and the coordinate system of the detector unit.

* * * * *